US012613240B2

(12) United States Patent
Aburaya et al.

(10) Patent No.: US 12,613,240 B2
(45) Date of Patent: *Apr. 28, 2026

(54) IMMUNOCHROMATOGRAPHY

(71) Applicant: FUJIFILM Corporation, Tokyo (JP)

(72) Inventors: Yoshihiro Aburaya, Ashigarakami-gun (JP); Naoyuki Nishikawa, Ashigarakami-gun (JP); Junichi Katada, Ashigarakami-gun (JP); Atsuhiko Wada, Ashigarakami-gun (JP); Dai Ujihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1086 days.

This patent is subject to a terminal disclaimer.

(21) Appl. No.: 17/690,177

(22) Filed: Mar. 9, 2022

(65) Prior Publication Data

US 2022/0196647 A1 Jun. 23, 2022

Related U.S. Application Data

(63) Continuation of application No. PCT/JP2020/024691, filed on Jun. 24, 2020.

(30) Foreign Application Priority Data

Sep. 30, 2019 (JP) ................................. 2019-178730

(51) Int. Cl.
*G01N 33/543* (2006.01)
*G01N 1/40* (2006.01)

(52) U.S. Cl.
CPC ....... *G01N 33/54313* (2013.01); *G01N 1/405* (2013.01); *G01N 33/54393* (2013.01)

(58) Field of Classification Search
None
See application file for complete search history.

(56) References Cited

U.S. PATENT DOCUMENTS 9,617,587 B1 * 4/2017 Miller ................ G01N 21/6428
2011/0287446 A1 11/2011 Kanda et al.
(Continued)

FOREIGN PATENT DOCUMENTS

CN 105116146 A 12/2015
JP 2007-85929 A 4/2007
(Continued)

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2020/024691, dated Apr. 14, 2022, with an English translation.
(Continued)

*Primary Examiner* — Rebecca M Giere
(74) *Attorney, Agent, or Firm* — Birch, Stewart, Kolasch & Birch, LLP

(57) ABSTRACT

An immunochromatography including steps of mixing an antigen-containable specimen and modified magnetic particles, which are magnetic particles modified with a monoclonal antibody X; collecting the magnetic particles from the mixture using magnetism; dissociating the modified magnetic particles to obtain an antigen-containing solution; neutralizing the antigen-containing solution to obtain a neutralized antigen-containing solution; spreading gold particle composite bodies on an insoluble carrier having a reaction site at which a monoclonal antibody Z has been immobilized, wherein the gold particle composite body is a composite body of the antigen and a modified gold particle which is a gold particle modified with a monoclonal antibody Y; capturing the gold particle composite bodies at the reaction site; and silver-amplifying the gold particle composite body, in which the antibody X and the antibody Y are (Continued)

different from each other, and the antibody X and the antibody Z are different from each other.

18 Claims, 1 Drawing Sheet

(56) References Cited

U.S. PATENT DOCUMENTS

| | | |
|---|---|---|
| 2013/0084580 A1 | 4/2013 | Wada et al. |
| 2014/0087367 A1 | 3/2014 | Wada |
| 2014/0154713 A1 | 6/2014 | Mizuno et al. |

FOREIGN PATENT DOCUMENTS

| | | |
|---|---|---|
| JP | 2010-60416 A | 3/2010 |
| JP | 2014-66674 A | 4/2014 |
| JP | 5728453 B2 | 6/2015 |
| JP | 2016-90570 A | 5/2016 |
| WO | WO 2010/092958 A1 | 8/2010 |
| WO | WO 2012/173002 A1 | 12/2012 |

OTHER PUBLICATIONS

International Search Report (Form PCT/ISA/210) for International Application No. PCT/JP2020/024691, dated Sep. 29, 2020, with an English translation.

Extended European Search Report for corresponding European Application No. 20871388.3, dated Nov. 4, 2022.

Fisher et al., "A combined immunomagnetic separation and lateral flow method for a sensitive on-site detection of *Bacillus anthracis* spores—assessment in water and dairy products," Letters in Applied Microbiology, vol. 48, 2009, pp. 413-418.

Koivunen et al., "Principles of Immunochemical Techniques Used in Clinical Laboratories," LabMedicine, vol. 37, No. 8, 2006, pp. 490-497.

Liu et al., "A modified lateral flow immunoassay for the detection of trace aflatoxin M1 based on immunomagnetic nanobeads with different antibody concentrations," Food Control, vol. 51, 2015, pp. 218-224.

Razo et al., "Double-enhanced lateral flow immunoassay for potato virus X based on a combination of magnetic and gold nanoparticles," Analytica Chimica Acta, vol. 1007, 2018, pp. 50-60.

Chinese Office Action and Search Report for corresponding Chinese Application No. 202080062167.4, dated Mar. 28, 2025, with English translation.

Zhang et al., "Rapid detection of Enterobacter cloacae by immunomagnetic separation and a colloidal gold-based immunochromatographic assay," RSC Advances, vol. 6, 2016, pp. 1279-1287.

Chinese Office Action for corresponding Chinese Application No. 202080062167.4, dated Sep. 8, 2025, with English translation.

Chinese Office Action for corresponding Chinese Application No. 202080062167.4, dated Nov. 26, 2025, with English translation.

* cited by examiner

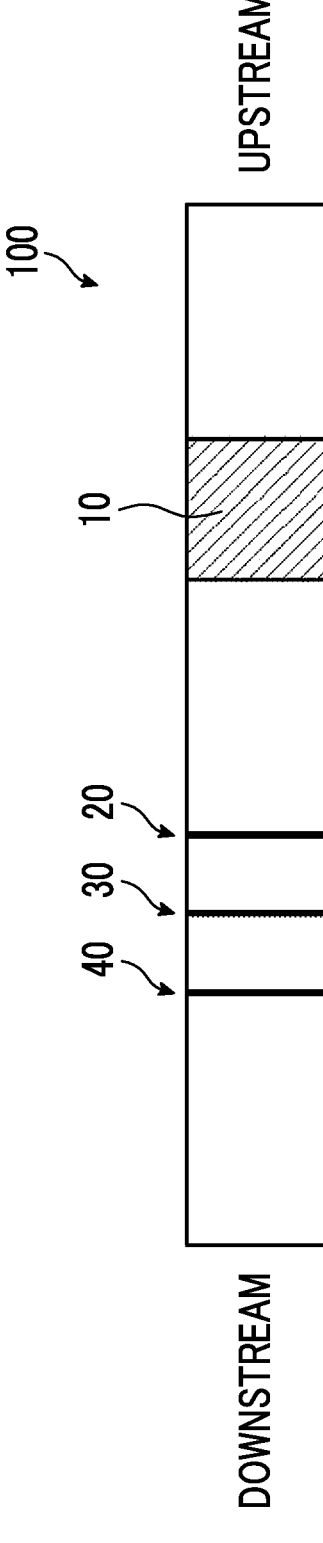

IMMUNOCHROMATOGRAPHY

CROSS-REFERENCE TO RELATED APPLICATIONS

This application is a Continuation of PCT International Application No. PCT/JP2020/024691 filed inn Jun. 24, 2020, which claims priority under 35 U.S.C. §119(a) to Japanese Patent Application No. 2019-178730 filed on Sep. 30, 2019. Each of the above application(s) is hereby expressly incorporated by reference, in its entirety, into the present application.

BACKGROUND OF THE INVENTION

1. Field of the invention

The present invention relates to immunochromatography.

2. Description of the Related Art

Immunochromatography is frequently used these days since the operation is easy and measurement can be carried out in a short time.

For example, in a case where an antigen such as influenza virus is detected by immunochromatography, the following operation is carried out.

First, a label modified with an antibody (labeled antibody) is prepared and mixed with a specimen containing an antigen. The labeled antibody binds to an antigen, whereby composite bodies are formed. In this state, in a case where these composite bodies are spread on an insoluble carrier having a detection line (a test line) onto which an antibody that specifically reacts with an antigen is applied, the composite bodies react with the antibody on the detection line and are captured, and detection is confirmed visually or in other manners.

Examples of such immunochromatography include the method disclosed in JP5728453B.

SUMMARY OF THE INVENTION

These days, an hnmunodiagnostic method having higher sensitivity is desired, and regarding the immunochromatography, there is also a demand for a method having higher sensitivity than the method in the related art (for example, the method disclosed in JP5728453B).

In consideration the above circumstances, an object of the present invention is to provide immunochromatography having high detection sensitivity.

As a result of diligent studies on the above-described problems, inventors of the present invention have found that the above object can be achieved by carrying out a predetermined pretreatment using magnetism and changing the kind of the monoclonal antibody that is used in each step, That is, the inventors of the present invention have found that the object can be achieved by the following configurations.

(1) Immunochromatography Comprising a mixing step of mixing an antigen-containable specimen and modified magnetic particles, which are magnetic particles modified with a monoclonal antibody X having a specific affinity to the antigen, to obtain a mixture containing magnetic particle composite bodies which are composite bodies of the antigen and the modified magnetic particle;

a collection step of collecting magnetic particles in the mixture containing the magnetic particle composite bodies using magnetism;

a dissociation step of dissociating the modified magnetic particles from the magnetic particle composite body to obtain an antigen-containing solution by mixing the magnetic particles collected in the collection step with a dissociation solution which is an acidic or alkaline solution;

a neutralization step of neutralizing the antigen-containing solution using a neutralization solution to obtain a neutralized antigen-containing solution;

a spreading step of spreading gold particle composite bodies on an insoluble carrier having a reaction site at which a. monoclonal antibody Z capable of binding to the antigen has been immobilized, in a state where the gold particle composite body which is a composite body of the antigen in the neutralized antigen-containing solution and a modified gold particle which is a gold particle modified with a monoclonal antibody Y capable of binding to the antigen;

a capturing step of capturing the gold particle composite bodies at the reaction site of the insoluble carrier, and a silver amplification step of silver-amplifying the gold particle composite body captured in the capturing step, in which the monoclonal antibody X and the monoclonal antibody Y are different from each other, and the monoclonal antibody X and the monoclonal antibody Z are different from each other, (2) The immunochromatography according to (1), in which the monoclonal antibody X, the monoclonal antibody Y, and the monoclonal antibody Z are all different from each other.

(3) The immunochromatography according to (1) or (2), in which the dissociation solution is a dissociation solution which is an acidic or alkaline solution, where an amount of the dissociation solution is smaller than the antigen-containable specimen.

(4) The immunochromatography according to (3), in which a. ratio of the dissociation solution to the antigen-containable specimen is $\frac{1}{5}$ or less in terms of mass ratio.

(5) The immunochromatography according to any one of (1) to (4), in which the dissociation solution contains NaOH or HCl.

(6) The immunochromatography according to any one of (1) to (5), in which the neutralization solution contains HCl and at least one selected from the group consisting of tricine, Tris, HEPES, acetamidoglycine, glycinamide, and vicine, or contains NaOH and at least one selected from the group consisting of tricine, Tris, HEPES, acetamidoglycine, glycinamide, and vicine.

(7) The immunochromatography according to any one of (1) to (6), in which a particle diameter of the magnetic particle before modification is 0.05 μm to 10 μm.

As described below; according to the present invention, it is possible to provide immunochromatography having high detection sensitivity.

BRIEF DESCRIPTION OF THE DRAWINGS

FIG. 1 is a schematic view illustrating an aspect of an insoluble carrier that is used in a method according to the embodiment of the present invention.

DESCRIPTION OF THE PREFERRED EMBODIMENTS

Immunochromatography according to the embodiment according to the embodiment of the present invention will be described below.

In the present specification, the numerical value range indicated by using "to" means a range including the numerical values before and after "to" as the lower limit value and the upper limit value, respectively, In addition, in the present specification, one kind of each component may be used alone, or two or more kinds thereof may be used in combination. In a case where two or more kinds of each component are used in combination, a content of the component indicates a total content unless otherwise specified.

Further, in the present specification. "the detection sensitivity and the signal/noise ratio (the S/N ratio) are further improved" is also described as "the effects and the like of the present invention are more excellent".

The immunochromatography according to the embodiment of the present invention (hereinafter, also referred to as "the method according to the embodiment of the present invention") is immunochromatography including;

a mixing step of mixing an antigen-containable specimen and modified magnetic particles, which are magnetic particles modified with a monoclonal antibody X having a specific affinity to the antigen, to obtain a mixture containing magnetic particle composite bodies which are composite bodies of the antigen and the modified magnetic particle;

a collection step of collecting magnetic particles in the mixture containing the magnetic particle composite bodies using magnetism;

a dissociation step of dissociating the modified magnetic particles from the magnetic particle composite body to obtain an antigen-containing solution by mixing the magnetic particles collected in the collection step with a dissociation solution which is an acidic or alkaline solution;

a neutralization step of neutralizing the antigen-containing solution using a neutralization solution to obtain a neutralized antigen-containing solution;

a spreading step of spreading gold particle composite bodies on an insoluble carrier having a reaction site at which a monoclonal antibody Z capable of binding to the antigen has been immobilized, in a state where the gold particle composite body which is a composite body of the antigen in the neutralized antigen-containing solution and a modified gold particle which is a gold particle modified with a monoclonal antibody Y capable of binding to the antigen;

a capturing step of capturing the gold particle composite bodies at the reaction site of the insoluble carrier, and a silver amplification step of silver-amplifying the gold particle composite body captured in the capturing step, in which the monoclonal antibody X and the monoclonal antibody Y are different from each other, and.

the monoclonal antibody X and the monoclonal antibody Z are different from each other.

As described above, in the method according to the embodiment of the present invention, the predetermined pretreatment (the mixing step, the collection step, the dissociation step, and the neutralization step) using magnetism is carried out, and the kind of the monoclonal antibody that is used in a specific step is changed to a different kind.

It is presumed that since the method according to the embodiment of the present invention has such a configuration, the above effects can be obtained. In particular, it is conceived that the method of the present invention is characterized in that the monoclonal antibody X that is used in the above pretreatment is different from the monoclonal antibody Y and/or monoclonal antibody Z that is used in the spreading step.

From the studies by inventors of the present invention, it has been known that in a case where an antigen is reacted with magnetic particles (modified magnetic particles) modified with a monoclonal antibody, and after an operation such as concentration, the modified magnetic particles are dissociated. to obtain an antigen-containing solution (particularly, an antigen-concentrated solution), there is a case where the dissociated modified magnetic particles remain in the solution and inhibit the antigen-antibody reaction in the immunochromatography.

The method according to the embodiment of the present invention is based on the above findings. That is, in the method according to the embodiment of the present invention, the monoclonal antibody that is used in the above pretreatment and the monoclonal antibody that is used in the immunochromatography (the spreading step) are different from each other. As a result, it is presumed that even in a case where the dissociated modified magnetic particles (the magnetic particles modified with a monoclonal antibody) react with the antigen again, a high detection sensitivity can be obtained without inhibiting the antigen-antibody reaction in the immunochromatography.

Hereinafter, each of the steps included in the method according to the embodiment of the present invention will be described. It is noted that the steps from the mixing step to the neutralization step are also collectively referred to as a "magnetic particle process".

Mixing Step

The mixing step is a step of mixing an antigen-containable specimen and modified magnetic particles, which are magnetic particles modified with a monoclonal antibody X having a specific affinity to the antigen, to obtain a mixture containing magnetic particle composite bodies which are composite bodies of the antigen and the modified magnetic particle.

Specimen

The specimen that is used in the mixing step is not particularly limited as long as it is an antigen-containable specimen. Examples of such a specimen include a biological specimen, particularly a biological specimen of animal origin (particularly, of human origin) such as a body fluid (for example, blood, serum, plasma, spinal fluid, tear fluid, sweat, urine, pus, runny nose, or sputum) or excrement (for example, feces), an organ, a tissue, a mucous membrane or skin, a scraped test sample (a swab) that is conceived to contain these substances, a mouthwash, and an animal and a plant themselves or a dried substance thereof.

Antigen

Examples of the antigen include a fungus, a bacterium (for example, tubercle bacillus or lipoarabinomannan (LAM) included in the tubercle bacillus), a virus (for example, an influenza virus), and a nuclear protein thereof LAM is a major antigen in tuberculosis and a glycolipid which is a major constitutional component of the cell membrane and the cell wall.

The antigen is preferably a virus or LAM, more preferably a virus, and still more preferably an influenza virus, due to the reason that the effects and the like of the present invention are more excellent.

Pretreatment of Specimen

Regarding the above specimen, it is possible to use the specimen as it is or in a form of an extraction solution obtained by extracting the antigen using an appropriate solvent for extraction, in a form of a diluent solution obtained by diluting an extraction solution with an appropriate diluent, or in a fomi in which an extraction solution has been concentrated by an appropriate method.

As the solvent for extraction, it is possible to use a solvent (for example, water, physiological saline, and a buffer solution) that is used in a general immunological analysis method, or a water-miscible organic solvent with which a direct antigen-antibody reaction can be carried out by being diluted with such a solvent.

Modified Magnetic Particle

The modified magnetic particle is a magnetic particle modified with the monoclonal antibody X having a specific affinity to the antigen.

Magnetic Particle

A material of the magnetic particles is not particularly limited as long as it is a material having magnetic properties, and specific examples thereof include iron, cobalt, nickel, oxides thereof, ferrite, alloys thereof. Among them, iron oxide is preferable due to the reason that the effects and the like of the present invention are more excellent.

The magnetic particle may be a particle obtained by molding only a material having magnetic properties into a particle shape. Alternatively, the magnetic particle may be a particle of which the surface has been coated with a polymer (such as polystyrene or silica gel) or the like and which has a material having magnetic properties as a core, or may be a particle of which the surface has been coated using a material having magnetic properties and which has a polymer or the like as a core.

Particle Diameter

The particle diameter of the magnetic particle is not particularly limited; however, it is preferably 0.05 μm to 10 μm. and more preferably to 0.1 μm to 5 μm due to the reason that the effects and the like of the present invention are more excellent.

The particle diameter can be measured with a commercially available particle diameter distribution meter or the like. As a method of measuring the particle size distribution, optical microscopy, confocal laser microscopy, electron microscopy, atomic force microscopy, static light scattering method, laser diffraction method, dynamic light scattering method, centrifugal sedimentation method, electric pulse measurement method, chromatography method, ultrasonic attenuation method, and the like are known, and apparatuses corresponding to the respective principles are commercially available. As the method of measuring a particle diameter, a dynamic light scattering method can be preferably used due to the particle diameter range and the ease of measurement. Examples of the commercially available measuring device using dynamic light scattering include NANOTRAC UPA (Ni.kkiso Co., Ltd.), a dynamic light scattering type particle size distribution measuring device LB-550 (HORIBA, Ltd.), and a Fiber-Optics Particle Analyzer FPAR-I000 (Otsuka Electronics Co., Ltd.). In the present invention, the average particle size is obtained as a value of a median diameter (d=50) measured at a measurement temperature of 25° C.

Monoclonal Antibody X:

The monoclonal antibody X is a monoclonal antibody having a specific affinity to the above antigen and is a monoclonal antibody different from the monoclonal antibody Y and the monoclonal antibody Z described later.

As the monoclonal antibody, it is possible to use, for example, a monoclonal antibody obtained by cell fusion using spleen cells of an animal immunized with an antigen, or a fragment thereof [for example, $F(ab')_2$, Fab, Fab', or Fv]. The preparation of these antibodies can be carried out by a conventional method.

Method of Manufacturing Modified Magnetic Particle

The method of manufacturing the modified magnetic particle is not particularly limited, and a known method can be used. Examples thereof include a method of activating magnetic particles with 1-ethyl-3-(3-dimethylaminopropyl) carbodiimide (EDC) to carry the monoclonal antibody X on the magnetic particle.

Mixing

In the mixing step, the specimen and the modified magnetic particles are mixed.

As a result, in a case where the specimen contains an antigen, the antigen in the specimen reacts with the monoclonal antibody X having a specific affinity to the antigen of the modified magnetic particle, and thereby a composite body of the antigen and the modified magnetic particle is formed in the specimen. On the other hand, in a case where the specimen does not contain an antigen, the composite body is not formed.

Collection Step

The collection step is a step of collecting magnetic particles in the mixture containing the magnetic particle composite body after the ahove-described mixing step by using magnetism.

Here, "collecting magnetic particles in the mixture" means "collecting the magnetic particle composite bodies in the mixture as well as the magnetic particles (unmodified magnetic particles) and the modified magnetic particles remaining in the mixture".

The method of collecting magnetic particles in the mixture after the mixing step by using magnetism is not particularly limited. Examples thereof include a method of placing the mixture after the mixing step in a conical tube installed on a magnetic stand, collecting the magnetic particle composite bodies with magnetism, and then removing the excess specimen.

Dissociation Step

The dissociation step is a step of dissociating the modified magnetic particles from the magnetic particle composite body to obtain an antigen-containing solution by mixing the magnetic particles collected in the collection step described above with a dissociation solution which is an alkaline or acidic solution.

In the dissociation step, the modified magnetic particles are dissociated from the magnetic particle composite bodies (the composite bodies of the antigen and the modified magnetic particles) by the dissociation solution, and they are separated into the antigen and the modified magnetic particles. As a result, an antigen-containing solution that is a dissociation solution containing the antigen is obtained.

Dissociation Solution

The dissociation solution is not particularly limited as long as it is an alkaline or acidic solution.

The alkaline solution is not particularly limited; however, specific examples thereof include an aqueous NaOH solution and an aqueous KOH solution. Among them, an aqueous NaOH solution is preferable due to the reason that the effects and the like of the present invention are more excellent.

The acidic solution is not particularly limited; however, specific examples thereof include an aqueous HCl solution, an aqueous $H_2SO_4$ solution, and an aqueous $HNO_3$ solution, Among them, an aqueous HCl solution is preferable due to the reason that the effects and the like of the present invention are more excellent.

The dissociation solution is preferably an alkaline solution due to the reason that the effects and the like of the present invention are more excellent.

The dissociation solution preferably contains NaOH or HCl_ more preferably contains NaOH, and still more preferably an aqueous NaOH solution, due to the reason that the effects and the like of the present invention are more excellent.

Amount

The amount of the dissociation solution is not particularly limited; however, it is preferably an amount of the dissociation solution, which smaller than the amount of the "antigen-containable specimen" that is used in the above-described mixing step due to the reason that the effects and the like of the present invention are more excellent. In a case where the amount of the dissociation solution is smaller than the amount of the "antigen-containable specimen" that is used in the above-described mixing step, the concentration of the antigen in the dissociation solution is higher than the concentration of the antigen in the "antigen-containable specimen" that is used in the above-described mixing step. That is, the antigen-containing solution obtained by the dissociation step is a solution (an antigen-concentrated solution) in which the concentration of the antigen is concentrated.

The ratio of the dissociation solution to the "antigen-containable specimen" that is used in the above-described mixing step is preferably ⅕ or less, more preferably ¹⁄₁₀ or less, and still more preferably ¹⁄₂₀ or less in terms of mass ratio due to the reason that the effects and the like of the present invention are more excellent.

Neutralization Step

The neutralization step is a step of neutralizing the antigen-containing solution obtained in the above-described dissociation step by using a neutralization solution to obtain a neutralized antigen-containing solution.

The antigen-containing solution obtained in the dissociation step is usually alkaline or acidic since a dissociation solution which is an alkaline or acidic solution is used for the dissociation in the above-described dissociation step. On the other hand, in a case where an alkaline or acidic solution is used in the spreading step described later, the monoclonal antibody Y or monoclonal antibody Z described later may be modified, which leads to a decrease in detection sensitivity. For this reason, in the neutralization step, the neutralization solution is used to neutralize the antigen-containing solution.

Neutralization Solution

The neutralization solution is not particularly limited; however, it is possible to use, for example, a known buffer solution.

Due to the reason that the effects and the like of the present invention are more excellent, in a case where the dissociation solution that is used in the above-described dissociation step is an alkaline solution, the neutralization solution is preferable to contain HCl (particularly, 1M HCl) and at least one selected from the group consisting of tricine, Tris. 4-(2-hydroxyethyl)-1-piperazineethanesulfonic acid (HEPES), acetamidoglycine, glycinamide, and vicine, and in a case where the dissociation solution used in the dissociation step described above is an acidic solution, the neutralization solution is preferable to contain NaOH (particularly, 1M NaOH) and at least one selected from the group consisting of trieine, Tris, HEPES, acetamidoglycine, glycinamide, and vicine,

Spreading Step

The spreading step is a step of spreading gold particle composite bodies on an insoluble carrier having a reaction site at which a monoclonal antibody Z capable of binding to an antigen in the neutralized antigen-containing solution obtained in the neutralization step described above has been immobilized, in a state where the gold particle composite bodies which are composite bodies of the antigen and modified gold particles which are gold particles modified with a monoclonal antibody Y capable of binding to the antigen are formed.

Gold Particle Composite Body

As described above, in the spreading step, first, the gold particle composite body which is a composite body of the antigen in the neutralized antigen-containing solution obtained in the above-described neutralization step and a modified gold particle which is a gold particle modified with the monoclonal antibody Y capable of binding to the antigen is formed.

Modified Gold Particle

The modified gold particle is a gold particle modified with the monoclonal antibody Y capable of binding to an antigen.

Gold Particle

Gold particle is not particularly limited.

The gold particle acts as a catalyst that reduces silver ions in the silver amplification step described later.

The particle diameter of the gold particles is preferably 100 am or less, more preferably 50 nm or less, still more preferably 30 nm or less, and particularly preferably 15 nm or less, due to the reason that the effects and the like of the present invention are more excellent.

The lower limit of the particle diameter of the gold particles is not particularly limited; however, it is preferably 1 am or more, more preferably 2 nm or more, and still more preferably 5 nm or more, due to the reason that the effects and the like of the present invention are more excellent.

The particle diameter of the gold particle can be determined by the same method as the method for the magnetic particles described above.

Monoclonal Antibody Y

The monoclonal antibody Y is a monoclonal antibody capable of binding to the above antigen and is not particularly limited as long as it is a monoclonal antibody different from the above monoclonal antibody X.

Specific examples and the preferred aspect of the monoclonal antibody Y are the same as those of the monoclonal antibody X described above.

Method of Manufacturing Modified Gold Particle

The method of manufacturing the modified gold particle is not particularly limited, and a known method can be used. Examples thereof include a chemical bonding method such as a method in which an SH group is introduced into the monoclonal antibody Y, amd the fact that gold and an SH group are chemically bonded is utilized so that the SH bond of the antibody is cleaved to generate an Au—S bond on the Au surface when the antibody approaches gold particles, whereby the antibody is immobilized.

Insoluble Carrier

The above-described insoluble carrier is an insoluble carrier having a reaction site (a test line) at which the monoclonal antibody Z capable of binding to the antigen is immobilized. The insoluble carrier may have a plurality of test lines depending on the kinds of antigens (for example, a test line for influenza A type virus and a test line for influenza B type virus). In addition, the insoluble carrier may have a control line on the downstream side of the test line in order to check the spreading of the gold particle composite bodies. Further in a case where a reducing agent solution is used in the silver amplification step described later, a coloring reagent immobilization line may be provided downstream of the test line in order to detect the reducing agent solution.

Examples of the specific aspect of the insoluble carrier include a nitrocellulose membrane 100 as illustrated in FIG. 1, which has from the upstream side; a gold colloid holding pad 10, a test line 20, a control line 30, and a coloring reagent immobilization line 40, Here, the gold colloid holding pad 10 is a pad that holds gold particles (modified gold particles) modified with the monoclonal antibody Y, the test line 20 is a line on which the monoclonal antibody Z is immobilized, the control line 30 is a line for checking the spreading, and the coloring reagent immobilization line 40 is a line for detecting the reducing agent solution described later. Here, the upstream side and the downstream side mean descriptions intended to indicate the spreading from the upstream side to the downstream side at the time when gold particle composite bodies are spread.

The specific aspect of the insoluble carrier (or an immunochromatographic kit having the insoluble carrier) includes the insoluble carrier or the immunochromatographic kit disclosed in JP5728453B. In addition, the entire content of JP5728453B relating to the insoluble carrier and the immunochromatographic kit is incorporated in the present specification as a part of the disclosure of the present specification.

Insoluble Carrier

The insoluble carrier is preferably a porous carrier. In particular, due to the reason that the effects and the like of the present invention are more excellent, it is preferably a nitrocellulose film (a nitrocellulose membrane), a cellulose membrane, an acetyl cellulose membrane, a polysulfone membrane, a polyether sulfone membrane, a nylon membrane, a glass fiber, a non-woven fabric, a cloth, a thread, or the like is preferable, and a nitrocellulose film is more preferable.

Monoclonal Antibody Z

The monoclonal antibody Z is a monoclonal antibody capable of binding to the above antigen and is not particularly limited as long as it is a monoclonal antibody different from the above monoclonal antibody X.

Specific examples and the preferred aspect of the monoclonal antibody Z are the same as those of the monoclonal antibody X described above.

Spreading

The method of spreading gold particle composite bodies on an insoluble carrier having a test line in a state where the gold particle composite bodies are formed is not particularly limited; however, examples thereof include a method in which the above nitrocellulose membrane 100 (or an immunochromatographic kit having the nitrocellulose membrane 100) as illustrated in FIG. 1 is prepared, and the neutralized antigen-containing solution obtained in the above-described neutralization step is dropwise added onto a gold colloid holding pad and moved from the upstream side to the downstream side by using the capillary phenomenon as illustrated in FIG. 1.

Capturing Step

The capturing step is a step of capturing the gold particle composite bodies at the reaction site of the insoluble carrier.

As described above, since the monoclonal antibody Z capable of binding to an antigen is immobilized at the reaction site of the insoluble carder, the gold particle composite bodies (the composite bodies of an antigen and modified gold particles) spread on the insoluble carrier in the spreading step is captured at the reaction site (the test line) of the insoluble carrier.

In a case where a specimen does not contain an antigen, the gold particle composite body is not formed, and thus the composite body is not captured at the reaction site of the insoluble carrier.

Silver Amplification Step

The silver amplification step is a step of silver-amplifying the gold particle composite body captured in the capturing step.

The silver amplification step is a step of forming large silver particles in the gold particle composite body captured at the reaction site of the insoluble carrier by providing silver ions to the insoluble carrier after the capturing step. More specifically, it is a step in which silver ions are reduced using gold particles of the gold particle composite body as a catalyst to form silver particles (for example, a diameter of 10 μm or more).

This significantly improves the detection sensitivity of the captured gold particle composite body.

Suitable Aspect

The method of providing silver ions to the insoluble carrier after the capturing step is not particularly limited; however, it is preferably a method in which the following reducing agent solution and the following silver amplification solution are used, due to the reason that the effects and the like of the present invention are more excellent.

Further, in addition to the reducing agent solution and the silver amplification solution, a washing solution may be used to wash the composite body remaining on the insoluble carrier except for the specific binding reaction. The reducing agent solution may also serve as a washing solution.

Reducing Agent Solution

The reducing agent solution contains a reducing agent capable of reducing silver ions, As the reducing agent capable of reducing silver ions, any inorganic or organic material or a mixture thereof can be used as long as it can reduce silver ions to silver. Preferred examples of the inorganic reducing agent include a reducing metal salt and a reducing metal complex salt, of which the atomic valence is capable of being changed with a metal ion such as $Fe^{2+}$, $V^{2+}$, or $Ti^{3+}$. In a case where an inorganic reducing agent is used, it is necessary to remove or detoxify oxidized ions by complexing or reducing the oxidized ions. For example, in a system in which $Fe^{2+}$ is used as the reducing agent, a complex of $Fe^{3+}$, which is an oxide, is formed using citric acid or ethylenediaminetetraacetic acid (EDTA), and therefore detoxification is possible. In the present invention, it is preferable to use such an inorganic reducing agent, and as a more preferable aspect of the present invention, it is preferable to use a metal salt of $Fe^{2+}$ as the reducing agent.

It is also possible to use, as the reducing agent, a main developing agent (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), or leuco dyes) that is used in a wet-type light-sensitive silver halide photographic material, and other materials obvious to those who are skilled in the technology in the present field, such as a material disclosed in U.S. Pat. No. 6,020,117A.

As the reducing agent, an ascorbic acid reducing agent is also preferable. The useful ascorbic acid reducing agent includes ascorbic acid, an analog thereof, an isomer thereof, and a derivative thereof. Preferred examples thereof include D- or L-ascorbic acid and a sugar derivative thereof (for example, γ-lactoascorbic acid, glucoascorbic acid, fucoascorbic acid, glucoheptoascorbic acid, or maltoascorbic acid), a sodium salt of ascorbic acid, a potassium salt of ascorbic acid, isoascorbic acid (or L-erythroascorbic acid), a salt thereof (for example, an alkali metal salt, an ammonium salt, or a salt known in the related technical field), ascorbic acid of the enediol type, ascorbic acid of the enaminol type, ascorbic acid of the thioenol type. Particularly preferred examples thereof include D-, L-, or D,L-ascorbic acid (and an alkali metal salt thereof) or isoascorhic acid (or an alkali metal salt thereof), and a sodium salt is a preferred salt. A mixture of these reducing agents can be used as necessary.

Due to the reason that the effects and the like of the present invention are more excellent, the reducing agent solution is preferably allowed to flow so that the angle between the spreading direction in the spreading step and the spreading direction of the reducing agent solution is 0 degrees to 150 degrees, and more preferably allowed to flow so that the angle between the spreading direction in the spreading step and the spreading direction of the reducing agent solution is 0 degrees to 135 degrees.

Examples of the method of regulating the angle between the spreading direction in the spreading step and the spreading direction of the reducing agent solution include the method described in Examples of JP2009-150869A.

Silver Amplification Solution

The silver amplification solution is a solution containing a compound containing silver ions. As the compound containing silver ions, it is possible to use, for example, organic silver salts, inorganic silver salts, or silver complexes. Preferred examples thereof include silver ion-containing compounds having a high solubility in a solvent such as water, such as silver nitrate, silver acetate, silver lactate, silver butyrate, and silver thiosulfate. Silver nitrate is particularly preferable. The silver complex is preferably a silver complex in which silver is coordinated with ligands having a water-soluble group such as a hydroxyl group or a sulfone group, and examples thereof include silver hydroxythioether.

As the silver, the organic silver salt, the inorganic silver salt, or the silver complex is preferably contained in the silver amplification solution at a concentration of 0.001 mol/L to 5 mol/L, preferably 0.005 mol/L to 3 mol/L, and more preferably 0.01 mol/L to 1 mol/L.

Examples of the auxiliary agent of the silver amplification solution include a buffer, a preservative such as an antioxidant or an organic stabilizer, and a rate regulating agent. As the buffer, it is possible to use, for example, a buffer formed of acetic acid, citric acid, sodium hydroxide, or one of salts of these compounds, or formed of tris(hydroxymethyl)aminomethane, or other buffers that are used in general chemical experiments. These buffers are appropriately used to adjust the pH of the amplification solution to an optimum pH thereof. In addition, as the antifogging agent, an alkyl amine can be used as an auxiliary agent, and dodecyl amine is particularly preferable. In addition, a surfactant can be used for the intended purpose of improving the solubility of this auxiliary agent, and $C_9H_{19}$—$C_6H_4$—O—$(CH_2CH_2O)_{50}H$ is particularly preferable.

Due to the reason that the effects and the like of the present invention are more excellent, the silver amplification solution is preferably allowed to flow from the direction opposite to the spreading direction in the spreading step described above and more preferably allowed to flow so that the angle between the spreading direction in the spreading step and the spreading direction of the silver amplification solution is 45 degrees to 180 degrees.

Examples of the method of regulating the angle between the spreading direction in the spreading step and the spreading direction of the silver amplification solution include the method described in Examples of JP2009-150869A.

Monoclonal Antibody

As described above, the monoclonal antibody X and the monoclonal antibody Y are different from each other; and the monoclonal antibody X and the monoclonal antibody Z are different from each other.

The monoclonal antibody Y and the monoclonal antibody Z may be the same or different from each other; however, they are preferably different from each other due to the reason that the effects and the like of the present invention are more excellent. In this case, the monoclonal antibody X, the monoclonal antibody Y, and the monoclonal antibody Z are all different monoclonal antibodies.

It is preferable that the epitope of the monoclonal antibody X and the epitope of the monoclonal antibody Y are different from each other due to the reason that the effects and the like of the present invention are more excellent.

It is preferable that the epitope of the monoclonal antibody X and the epitope of the monoclonal antibody Z are different from each other due to the reason that the effects and the like of the present invention are more excellent.

The epitope of the monoclonal antibody Y and the epitope of the monoclonal antibody Z may be the same or different from each other; however, they are preferably different from each other due to the reason that the effects and the like of the present invention are more excellent. In this case, the epitope of the monoclonal antibody X, the epitope of the monoclonal antibody Y, and the epitope of the monoclonal antibody 7 are all different.

The difference in epitope between monoclonal antibodies can be confirmed by, for example, an enzyme-linked immuno-sorbent assay (ELISA).

EXAMPLES

Hereinafter, the present invention will be described in more detail with reference to Examples; however, the present invention is not limited thereto.

Preparation of Sample Solution

A sample solution (an antigen-containable specimen) was prepared using a Quick A-B "SEIKEN" negative/positive control solution (product number: 322968, manufactured by DENKA SEIKEN Co., Ltd.).

Specifically, the above positive control solution was subjected to serial 10-time dilutions with a phosphate buffered salts (PBS) buffer containing 1% by mass bovine serum albumin (BSA), and sample solutions (antigen-containable specimens) with the respective dilution rates were prepared.

The detection limit (the minimum detection sensitivity) obtained by the commercially available immunochromatographic detection kit "Capilia Flu A+B" (manufactured by Alfresa Pharma Corporation) was $\frac{1}{40}$ for both A type and B type.

Example 1

Immunochromatography of Example 1 was carried out as follows.

Mixing Step

Magnetic particles (Dynabeads MyOne-COOH, particle diameter: 1 μm, manufactured by Thermo Fisher Scientific, Inc.) manufactured by Thermo Fisher Scientific, Inc. were activated with 1-ethyl-3-(3-dimethylaminopropyl)carbodiimide (EDC), and an anti-influenza type A monoclonal antibody (Funakoshi Co., Ltd., #GTX629544) was carried on the magnetic particles to obtain modified magnetic particles which are magnetic particles modified with the anti-influenza. A type monoclonal antibody (the monoclonal antibody X).

The above sample solution (6 mL) was placed in a 15 mL conical tube, 1 mg of the above modified magnetic particles were placed therein, and the reaction was carried out with stirring for 40 minutes. in this manner, a mixture containing magnetic particle composite bodies, which are composite bodies of the influenza type A virus and the modified magnetic particles, was obtained.

Collection Step

After the reaction, the conical tube was installed on a magnet stand, and the magnetic particles (unmodified magnetic particles, modified magnetic particles, and magnetic particle composite bodies) were magnetically collected for 10 minutes. The excess sample solution was removed from the conical tube with a pipette (manufactured by Eppendorf) to collect the above magnetic particles (unmodified magnetic particles, modified magnetic particles, and magnetic particle composite bodies).

Dissociation Step

Immediately, 200 μL of an aqueous 50 mM NaOH solution (an alkaline solution) was added. After the addition, sonication treatment was carried out for 5 minutes followed by being allowed to stand for 60 minutes. In this manner, the modified magnetic particles were dissociated from the magnetic particle composite bodies. After being allowed to stand, the conical tube was installed on a magnet stand again, and the dissociated modified magnetic particles were magnetically collected for 10 minutes, and the supernatant solution (the influenza A type virus-containing solution) (the antigen-containing solution) was recovered.

Neutralization Step

The influenza A type virus-containing solution was neutralized using 10 μL of 10 mM Tris HCl as the neutralization solution to obtain a neutralized influenza A type virus-containing solution (a neutralized antigen-containing solution).

Spreading Step

The nitrocellulose membrane 100 as illustrated in FIG. 1 was prepared, which has from the upstream side; the gold colloid holding pad 10, the test line 20, the control line 30, and the coloring reagent immobilization line 40. The gold colloid holding pad 10 is a pad that holds gold colloids (modified gold particles) modified with an anti-influenza A type monoclonal antibody (Anti-Influenza A SPTN-5 7307, Medix Biochemica) (the monoclonal antibody Y), the test line 20 is a line on which the anti-influenza A type monoclonal antibody (Anti-Influenza A SPTN-5 7307, Mcdix Biochemical) (the monoclonal antibody Z) is immobilized, the control line 30 is a line for checking the spreading, and the coloring reagent immobilization line 40 is a line for detecting the reducing agent solution described later.

The above-described neutralized influenza A type virus-containing solution was dropwise added onto the gold colloid holding pad. As a result, gold particle composite bodies, which are composite bodies of the influenza A type virus in the solution and the gold colloid particles (modified gold particles) modified with the anti-influenza A type monoclonal antibody (the monoclonal antibody Y) in the gold colloid holding pad, were formed. In this state, the gold particle composite bodies were spread toward the downstream side of the nitrocellulose membrane.

Capturing Step

The gold particle composite.bodies that are spread in the spreading step is captured on the test line.

Silver Amplification Step

The silver amplification step was carried out as follows.

Preparation of Reducing Agent Solution 23.6 mL of an aqueous solution of 1 mol/L iron nitrate, which was produced by dissolving iron (III) nitrate nonahydrate (manufactured by FUJIFILM Wako Pure Chemical Corporation) in water, and 13.1 g of citric acid (manufactured by FUJIFILM Wako Pure Chemical Corporation) were dissolved in 290 g of water. After all of the substances were dissolved, 36 mL of nitric acid (10% by mass) was added thereto while stirring with a stirrer, 60.8 g of ammonium iron (II) sulfate hexahydrate (manufactured by FUJIFILM Wako Pure Chemical Corporation) was added thereto, and the resultant solution was used as the reducing agent solution.

Preparation of Silver Amplification Solution 8 mL of a silver nitrate solution (including 10 g of silver nitrate) and 24 mL of an aqueous solution of 1 MOH, iron nitrate were added to 66 g of water. Further, this solution was mixed with a solution obtained by dissolving 5.9 mL of nitric acid (10% by mass), 0.1 g of dodecyl amine (manufactured by FUJIFILM Wako Pure Chemical Corporation), and 0.1 of a surfactant $C_{12}H_{25}\text{-}C_6H_4\text{---}O\text{---}(CH_2CH_2O)_{50}H$ in 47.6 g of water in advance, and the resultant solution was used as the silver amplification solution.

Spreading of Reducing Agent Solution

In the nitrocellulose membrane, the reducing agent solution prepared as described above was allowed to flow from the same direction as that of the spreading step described above (from the upstream side).

Spreading of Silver Amplification Solution

After the coloring reagent immobilization line was discolored, the silver amplification solution prepared as described above was allowed to flow from the direction opposite to the spreading direction (from the downstream side) in the spreading step. In this manner, the gold particle composite body captured on the test line was silver amplified.

Evaluation

The coloration of the test line was visually checked, and the lowest dilution rate (the minimum detection sensitivity)

at which coloration was confirmed was investigated. The results are shown in Table 1. It means that as the minimum detection sensitivity is lower, an antigen can be detected even in a specimen having a low antigen concentration, which means the detection sensitivity is high.

Comparative Example 1

Immunochromatography was carried out and evaluated according to the same procedure as in Example 1 except that without carrying out the steps from the mixing step to the neutralization step, the above-described sample solution itself was used instead of the neutralized influenza A type virus-containing solution in the spreading step. The results are shown in Table 1.

Comparative Example 2

Immunochromatography was carried out and evaluated according to the same procedure as in Example 1 except that as the monoclonal antibody X, an anti-influenza A type monoclonal antibody (Anti-Influenza A SPTN-5 7307, Mcdix Biochemica) was used instead of the anti-influenza A type monoclonal antibody (Funakoshi Co., Ltd, #GTX629544 ). The results are shown in Table 1. In Comparative Example 2, the monoclonal antibody X and the monoclonal antibody Y are the same, and the monoclonal antibody X and the monoclonal antibody Z are the same.

TABLE 1

|  | Comparative Example 1 | Comparative Example 2 | Example 1 |
| --- | --- | --- | --- |
| Minimum detection sensitivity | 1/20 | 1/1600 | 1/4800 |

As can be seen from Table 1, as compared with Comparative Example 1 in which the magnetic particle process was not carried out and Comparative Example 2 in which the magnetic particle process was carried out and the monoclonal antibody X and the monoclonal antibody Y were the same and the monoclonal antibody X and the monoclonal antibody Z were the same, Example 1 in which the magnetic particle process was carried out but the monoclonal antibody X and the monoclonal antibody Y were different from each other and the monoclonal antibody X and the monoclonal antibody Z were different from each other exhibited high detection sensitivity.

In addition, when immunochromatography was carried out in the same manner as in Example 1 and Comparative Examples 1 and 2 described above except that as the monoclonal antibody (the monoclonal antibody X, the monoclonal antibody 1, or the monoclonal antibody Z), an anti-influenza B type monoclonal antibody was used instead of the anti-influenza A type monoclonal antibody, the same tendency as in Table I was observed.

EXPLANATION OF REFERENCES

10: gold colloid holding pad
20: test line
30: control line
40 coloring reagent immobilization line
100: nitrocellulose membrane

What is claimed is:

1. Immunochromatography method comprising:

mixing an antigen-containable specimen and modified magnetic particles, which are magnetic particles modified with a monoclonal antibody X having a specific affinity to the antigen, to obtain a mixture containing magnetic particle composite bodies which are composite bodies of the antigen and the modified magnetic particle;

collecting the magnetic particle composite bodies in the mixture using magnetism;

dissociating the modified magnetic particles from the magnetic particle composite body to obtain an antigen-containing solution by mixing the collected magnetic particle composite bodies with a dissociation solution which is an acidic or alkaline solution;

neutralizing the antigen-containing solution using a neutralization solution to obtain a neutralized antigen-containing solution;

spreading gold particle composite bodies on an insoluble carrier, in a state where the gold particle composite bodies which are composite bodies of the antigen and modified gold particles are formed, by adding dropwise the neutralized antigen-containing solution onto a gold colloid holding pad, which is a pad that holds the modified gold particles which are gold particles modified with a monoclonal antibody Y capable of binding to an antigen in the neutralized antigen-containing solution, of the insoluble carrier having the gold colloid holding pad and a reaction site at which a monoclonal antibody Z capable of binding to the antigen has been immobilized;

capturing the gold particle composite bodies at the reaction site of the insoluble carrier; and silver-amplifying the captured gold particle composite body, wherein the monoclonal antibody X and the monoclonal antibody Y are different from each other, and the monoclonal antibody X and the monoclonal antibody Z are different from each other.

2. The immunochromatography method according to claim 1, wherein the monoclonal antibody X, the monoclonal antibody Y, and the monoclonal antibody Z are all different from each other.

3. The immunochromatography method according to claim 1, wherein an amount of the dissociation solution is smaller than the antigen-containable specimen before mixing the antigen-containable specimen and the modified magnetic particles.

4. The immunochromatography method according to claim 2, wherein an amount of the dissociation solution is smaller than the antigen-containable specimen before mixing the antigen-containable specimen and the modified magnetic particles.

5. The immunochromatography method according to claim 3, wherein a ratio of the dissociation solution to the antigen-containable specimen is ⅕ or less in terms of mass ratio.

6. The immunochromatography method according to claim 4, wherein a ratio of the dissociation solution to the antigen-containable specimen is ⅕ or less in terms of mass ratio.

7. The immunochromatography method according to claim 1, wherein the dissociation solution contains NaOH or HCl.

8. The immunochromatography method according to claim 2, wherein the dissociation solution contains NaOH or HCl.

9. The immunochromatography method according to claim 3, wherein the dissociation solution contains NaOH or HCl.

10. The immunochromatography method according to claim 4, wherein the dissociation solution contains NaOH or HCl.

11. The immunochromatography method according to claim 1, wherein the neutralization solution contains HCl and at least one selected from the group consisting of tricine, Tris, HEPES, acetamidoglycine, glycinamide, and vicine, or contains NaOH and at least one selected from the group consisting of tricine, Tris, HEPES, acetamidoglycine, glycinamide, and vicine.

12. The immunochromatography method according to claim 2, wherein the neutralization solution contains HCl and at least one selected from the group consisting of tricine, Tris, HEPES, acetamidoglycine, glycinamide, and vicine, or contains NaOH and at least one selected from the group consisting of tricine, Tris, HEPES, acetamidoglycine, glycinamide, and vicine.

13. The immunochromatography method according to claim 3, wherein the neutralization solution contains HCl and at least one selected from the group consisting of tricine, Tris, HEPES, acetamidoglycine, glycinamide, and vicine, or contains NaOH and at least one selected from the group consisting of tricine, Tris, HEPES, acetamidoglycine, glycinamide, and vicine.

14. The immunochromatography method according to claim 4, wherein the neutralization solution contains HCl and at least one selected from the group consisting of tricine, Tris, HEPES, acetamidoglycine, glycinamide, and vicine, or contains NaOH and at least one selected from the group consisting of tricine, Tris, HEPES, acetamidoglycine, glycinamide, and vicine.

15. The immunochromatography method according to claim 1, wherein a particle diameter of the magnetic particle before modification is 0.05 μm to 10 μm.

16. The immunochromatography method according to claim 2, wherein a particle diameter of the magnetic particle before modification is 0.05 μm to 10 μm.

17. The immunochromatography method according to claim 3, wherein a particle diameter of the magnetic particle before modification is 0.05 μm to 10 μm.

18. The immunochromatography method according to claim 4, wherein a particle diameter of the magnetic particle before modification is 0.05 μm to 10 μm.

* * * * *